(12) United States Patent
Van Putten et al.

(10) Patent No.: US 10,299,661 B2
(45) Date of Patent: May 28, 2019

(54) MEDICAL OPTICAL CONNECTOR SYSTEM

(71) Applicant: KONINKLIJKE PHILIPS N.V., Eindhoven (NL)

(72) Inventors: Eibert Gerjan Van Putten, 's-Hertogenbosch (NL); Johannes Joseph Hubertina Barbara Schleipen, Eindhoven (NL); Martinus Bernardus Van Der Mark, Best (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/571,542

(22) PCT Filed: May 24, 2016

(86) PCT No.: PCT/EP2016/061628
§ 371 (c)(1),
(2) Date: Nov. 3, 2017

(87) PCT Pub. No.: WO2016/193051
PCT Pub. Date: Dec. 8, 2016

(65) Prior Publication Data
US 2018/0140170 A1    May 24, 2018

(30) Foreign Application Priority Data
Jun. 3, 2015   (EP) .................................... 15170405

(51) Int. Cl.
*A61B 1/00* (2006.01)
*G02B 6/32* (2006.01)
(Continued)

(52) U.S. Cl.
CPC ...... *A61B 1/00126* (2013.01); *A61B 1/00013* (2013.01); *G02B 6/32* (2013.01);
(Continued)

(58) Field of Classification Search
CPC .... G02B 6/32; A61B 1/00013; A61B 1/00126
See application file for complete search history.

(56) References Cited

U.S. PATENT DOCUMENTS

| 5,329,936 A | 7/1994 | Lafferty et al. |
| 5,371,814 A * | 12/1994 | Ames ....................... G02B 6/32 |
| | | 385/25 |

(Continued)

FOREIGN PATENT DOCUMENTS

WO    2012124092 A1    9/2012

OTHER PUBLICATIONS

Marcuse, D. "Loss Analysis of Single-Mode Fiber Splices", American Telephone and Telegraph Company, The Bell System Technical Journal, vol. 56, No. 5, May-Jun. 1977.
(Continued)

*Primary Examiner* — Daniel Petkovsek (57) ABSTRACT

The present invention relates to a medical optical connector for reversibly connecting two associated optical fibers (12, 14) for use in medical interventions, comprising a fiber carrying unit (16, 18) for inserting an end portion of at least one of the associated optical fibers (12, 14), and an optical arrangement (20) for interacting with a light beam from one of the associated optical fibers (12, 14) and conducting the light beam to the other one of the associated optical fibers (12, 14) in a connected state of the medical optical connector, the optical arrangement (20) comprising at least two gradient index elements (22a, 22b) and an additional optical element (23, 25) arranged between the at least two gradient index elements, wherein the additional optical element provides for a sterility barrier between the associated fibers (12, 14).

18 Claims, 5 Drawing Sheets

(51) Int. Cl.
  *A61B 90/00* (2016.01)
  *A61B 17/00* (2006.01)
  *A61B 34/20* (2016.01)

(52) U.S. Cl.
  CPC ..... *A61B 1/00117* (2013.01); *A61B 17/00234* (2013.01); *A61B 90/37* (2016.02); *A61B 2034/2061* (2016.02)

(56) References Cited

U.S. PATENT DOCUMENTS

| | | | |
|---|---|---|---|
| 5,949,929 A | | 9/1999 | Hamm |
| 6,373,048 B1 * | | 4/2002 | Tschanun ............ G01C 19/721 250/231.12 |
| 6,847,770 B2 * | | 1/2005 | Kittaka ................ C03C 21/002 385/124 |
| 7,031,567 B2 * | | 4/2006 | Grinderslev ............ G02B 6/32 385/34 |
| 9,408,527 B2 | | 8/2016 | Hoeg et al. |
| 9,636,005 B2 * | | 5/2017 | Yoshino ................... A61B 1/06 |
| 2010/0329609 A1 | | 12/2010 | Shimotsu |
| 2011/0184244 A1 | | 7/2011 | Kagaya et al. |
| 2016/0038030 A1 | | 2/2016 | Smith et al. |

OTHER PUBLICATIONS

Grinteh GmbH. Gradient Index Optics Technology, Product Information. , http://www.grintech.de/downloads.html?file=ti_files/content/downloads/GRIN_CATALOG.pdf, date downloaded: Feb. 19, 2015, pp. 16.
Hecht, Eugene, Optics, 4th Ed, Addison Wesley, 1987, pp. 274-275.

* cited by examiner

FIG. 9

MEDICAL OPTICAL CONNECTOR SYSTEM

CROSS-REFERENCE TO PRIOR APPLICATIONS

This application is the U.S. National Phase application under 35 U.S.C. § 371 of International Application Serial No. PCT/EP2016/061628, filed on May 24, 2016, which claims the benefit of European Patent Application No. EP15170405.3, filed on Jun. 3, 2015. These applications are hereby incorporated by reference herein.

FIELD OF THE INVENTION

The present invention relates to a medical optical connector system and method for reversibly connecting two associated optical fibers. It finds applications in interventional medical devices and interventional treatment procedures, in particular in optical interrogation techniques in minimally invasive medical interventions.

BACKGROUND OF THE INVENTION

In minimally invasive medical intervention, interventional devices such as needles, guide wires, sheaths and catheters are inserted in a patient in order to find and measure the relevant anatomy of the patient on one hand and to treat or place a medical instrument such as a stent on the other hand. In such medical applications, the part of the interventional devices inserted into the patient either must be sterile during the entire treatment duration or should only be contaminated with fluids and tissue from the patient himself.

When the interventional device, in particular a needle, guide wire or catheter, is equipped with a sensor or activator, one or more connections, for instance electrical wires or optical fibers, must be made to transmit the information or power to or from a controller or interrogator placed in the non-sterile zone away from the patient. This means that somewhere along the information/power transmission line, the sterile zone meets the non-sterile zone. Consequently, a proper management of sterility is required.

This sterility management is also important for Optical Shape Sensing (OSS), which uses backscattered light, for instance infrared (IR) light, at distributed positions along an optical sensor to determine the strain along the length of this sensor. From this strain measurement the corresponding shape of that optical sensor can be reconstructed. When the optical sensor is incorporated into a flexible medical device such as a guide wire or a catheter, this technology can provide the shape of the medical device within the patient body. The Optical Shape Sensing (OSS) technology is also called Fiber-optical RealShape (FORS) technology.

During an OSS procedure, an optical connection needs to be established between an optical sensor on one hand, which is inserted in a patient and must be sterile; and a patch cord, a controller or an interrogator on the other hand, which is placed in the non-sterile zone away from the patient. Upon making the optical connection, the sterile proximal end of the optical sensor comes in contact with a non-sterile patch cord, a mating sleeve of a controller or interrogator, thereby becoming non-sterile. During a medical procedure a sterility problem may arise when the optical waveguide connected to the patch cord, controller or interrogator needs to be disconnected and the now non-sterile proximal end of the optical sensor needs to enter the sterile zone or when medical devices such as catheters, guide wires or sheaths need to slide over the optical sensor. The optical sensor or optical waveguide are for instance optical fibers. The medical device sliding over the optical sensor and having direct contact with the inner body of the patient therefore transports any contamination into the body of the patient.

One way to solve the sterility problem is to introduce a sterile barrier between the sterile proximal end of the optical sensor and the non-sterile patch cord, controller or interrogator. U.S. Pat. No. 5,949,929 discloses a rotary optical connection system for use with a fiber-optic imaging catheter. The system comprises a stationary sterile shield. The stationary sterile shield is made of a biocompatible injection-molded elastomer such as polyethylene, polyolefin, PEBAX. Further, the sterile shield disclosed therein does not protect the optical interfaces at the connection.

In case the sterile barriers are placed in between the optical fibers, the system may be disadvantageous due to high optical insertion losses. In order to reduce the optical insertion loss, the sterile barrier needs to be made very thin so that it becomes rather fragile and prone to rupture. Further, the goal of lowering the insertion loss also poses stringent requirements on the relative alignment of the optical fibers on both the sterile and the non-sterile sides. In particular, the relative alignment has to be a fraction of the mode field diameter which is in the order of several micrometers.

EP 2 267 501 A2 discloses an optical fiber connector and endoscope system, wherein the optical fiber connector comprises two gradient-index fibers functioning as a collimator lens, with an air gap between the two gradient-index fibers.

WO 2014/142958 A1 discloses an optical pressure sensor assembly comprising an optical connector using a gradient index lens.

SUMMARY OF THE INVENTION

It is an object of the present invention to provide a medical optical connector system and method for reversibly connecting two associated optical fibers that enable a sterility barrier between the associated optical fibers while providing higher mechanical stability and reducing the optical insertion losses between the optical fibers.

In a first aspect of the present invention a medical optical connector system for reversibly connecting two associated optical fibers is provided that comprises a fiber carrying unit for inserting an end portion of at least one of the associated optical fibers and an optical arrangement for interacting with a light beam from one of the associated optical fibers and conducting the light beam to the other one of the associated optical fibers in a connected state of the optical connector system, the optical arrangement comprising at least two gradient index elements and an additional optical element (23, 25) arranged between the at least two gradient index elements, wherein the additional optical element provides for a sterility barrier between the associated fibers.

In a further aspect of the present invention an optical system for optically coupling to an interventional medical device, wherein the optical system comprises two associated optical fibers, a medical optical connector for reversibly connecting the two associated optical fibers as described above.

In a further aspect of the present invention a method for reversibly connecting two associated optical fibers is provided that comprises inserting an end portion of at least one of the associated optical fibers into a fiber carrying unit, interacting with a light beam from one of the associated optical fibers and conducting the light beam to the other one of the associated optical fibers using an optical arrangement comprising at least two gradient index elements and arranging an additional optical element between the at least two gradient index elements, whereby the additional optical elements provides for a sterility barrier between the associated optical fibers.

Preferred embodiments of the invention are defined in the dependent claims. It shall be understood that the method has similar and/or identical preferred embodiments as the claimed medical optical system and as defined in the dependent claims.

The fiber carrying unit, which may comprise one or more ferrules, is configured to hold an end portion of one or both optical fibers, wherein the end portion of the optical fiber(s) can be inserted into the fiber carrying unit. This advantageously ensures a secure connection between the two optical fibers so that the end portion of the at least one optical fiber is prevented from being damaged.

The optical arrangement consists of the one or more optical elements which interact with a light beam transmitted by one of the two optical fibers and conduct the light beam to the other optical fiber, when the two optical fibers are connected by the medical optical connector. The one or more optical elements may be made of silica.

At the same time, the one or more optical elements also form a sterility barrier between the two associated optical fibers. Advantageously, the optical arrangement fulfills two technical functions simultaneously: providing an optical connection between the two associate optical fibers on one hand, and preventing the sterile side of two optical fibers from being contaminated by the non-sterile side, thereby alleviating the sterility problem in medical interventions.

Besides enabling a simpler construction, the present invention also achieves to increase the mechanical stability compared to the system known from the past. In particular, the stationary shield which is used as sterility barrier in the afore-mentioned U.S. Pat. No. 5,949,929 is made of an elastomer which is known for its elastic properties and mechanical deformability. While providing a sterility barrier, such an elastomer shield bares the disadvantage of being less stable. Consequently, misalignment between the two associated optical fibers is inevitable leading to insertion losses of the optical connection. In contrast, the present invention uses optical element(s) as sterility barrier which enables high mechanical stability and reduced insertion loss.

In addition, the optical arrangement comprises one or more gradient index (GRIN) elements. In particular, the optical arrangement may consist of only one optical element being a GRIN element; or alternatively of a plurality of optical elements, from which at least one is a GRIN element. Advantageously, the at least one GRIN element further increases the mechanical stability of the optical connection while being less sensitive to misalignment between the two associated optical fibers and/or between these and the optical arrangement.

The one or more optical elements may be one or more mirrors, lenses, optically transparent spacers and/or prisms. The fiber carrying unit may be one or more elements serving to at least partially encapsulate the end of one or both optical fibers and may in general be formed by various materials, e.g. polymers, metals or combinations thereof. At least one of the two associated optical fibers may be a multi-core optical fiber comprising a central core surrounded by one or more outer cores spiraling along the elongation of the central core.

In an advantageous embodiment, at least one gradient index element is includes in the sterility barrier. In this way, the one or more gradient index elements of the optical arrangement fulfill two technical functions simultaneously: providing an optical connection between the two optical fibers on one hand; and preventing the sterile side of the two optical fibers as well as the patient body from being contaminated on the other hand. Advantageously, the optical connection is built with higher mechanical stability and reduced insertion losses between the two optical fibers. Preferably, the GRIN element arranged to receive the optical fiber on the sterile side may be in direct contact with the optical fiber, e.g. having no spacing to the sterile optical fiber, thereby increasing the mechanical stability and reducing spurious reflections dramatically. This is particularly advantageous in applications where the optical sensors have to be read out interferometrically, such as during optical shape sensing (OSS). In this case the GRIN element should be sterile itself.

In another advantageous embodiment, the total pitch of the one or more gradient index elements is essentially equal to a positive integer divided by two. A pitch is the length of an optical element, in particular a lens, in units of the periodicity length of a periodic path travelled by a light beam propagating in the optical element. The total pitch is the sum of the individual pitch of each of the GRIN elements. Advantageously, the medical optical connector is more tolerant against misalignment between the two optical fibers and/or between the optical arrangement and the fiber carrying unit when the positive integer is equal to 2 or a multiple of 2, i.e. 2, 4, 6, . . . . Therefore, preferably, the positive integer is equal to 2 or a multiple of 2, i.e. 2, 4, 6, etc.

In another advantageous embodiment, where there are for example two GRIN elements, the pitch of each of the gradient index elements is essentially equal to the difference between a positive integer divided by two and one forth. Preferably, the total pitch of all GRIN elements is equal to a positive integer divided by two. The GRIN element, in particular a GRIN lens, may thus be realized as a light collimator being able to correct propagation directions of light beams due to misalignment between the components of the medical optical connector and/or the optical fibers. Advantageously, the medical optical connector is even more tolerant against misalignment. Further, the insertion loss between the two optical fibers is further reduced. The positive integers for at least two GRIN elements may be different.

In another advantageous embodiment, the numerical aperture of the one or more gradient index elements is equal to or higher than the larger one of the numerical apertures of the two associated optical fibers. The maximum amount of decentering between optical elements of the optical arrangement and/or between the optical arrangement and at least one optical fiber and/or between the two optical fibers depends on the numerical aperture of the one or more gradient index elements. Advantageously, the present invention enables a higher value of the maximum misalignment allowable in the optical connection. The misalignment between the GRIN lens and the optical fiber is preferably about or less than 1 μm.

In another advantageous embodiment, the one or more gradient index elements comprise one or more gradient index lenses and/or one or more gradient index fibers. Advantageously, the GRIN lenses and/or fibers provide a variety of optical connections between the associated optical fibers. Preferably, at least one GRIN lens is a GRIN rod lens. Further preferably, the refractive index of at least one GRIN lens increases or decreases along a radial direction perpendicular to the optical axis of the GRIN lens. The GRIN fiber may be a GRIN multimode fiber which enables transmitting multiple modes of light.

In another advantageous embodiment, at least two gradient index elements have different diameters. In this way, the medical optical connector can be built to fulfill a variety of size requirements during medical interventions. Further, the medical optical connector can be built with back-loadability, i.e. at least one side of the medical optical connector is integratable in a medical interventional device such as a guide wire, a sheath or a catheter. Preferably, at least one GRIN element has an outer diameter that is equal or smaller than the outer diameter of a guide wire or a catheter.

In another advantageous embodiment, one of the gradient index elements is integratable in an interventional medical device, in which an end portion of one of the two associated optical fibers is insertable. This advantageously enables the back-loadability of the medical optical connector, wherein misalignment between the optical arrangement and the optical fiber inserted in the interventional medical device is further reduced. At least a proximal end portion of the interventional medical device, such as a guide wire, may form a part of the fiber carrying unit. The integratable gradient index element may be provided with a transparent material, such as a transparent glue, at its proximal end opposite to the interventional medical device or facing the non-sterile side. In particular, the use of the transparent glue makes it possible to fill up the space due to the length difference between the GRIN element and the space within the interventional device for accommodating the GRIN element, so that the integratable GRIN element may be chosen within a length tolerance. In case the GRIN element is configured to collimate the light from the optical fiber, the image taken via the medical device is advantageously distortionless.

Preferably, another one of the gradient index elements is received by the fiber carrying unit, in which an end portion of the other one of the two associated optical fibers is insertable. Further preferably, the other gradient index element may be a disposable element which serves as a sterility barrier. Preferably, the two GRIN elements, in particular GRIN lenses, directly contact each other, which advantageously increases the mechanical stability of the medical optical connector.

In another advantageous embodiment, an additional optical element of the optical arrangement is arranged between two gradient index elements, the sterility barrier including the additional optical element and/or at least one of the two gradient index elements. Advantageously, the additional optical element reduces misalignment between the two GRIN elements. Preferably, the additional optical element comprises a glass plate, a membrane layer and/or a prism. In particular, the additional optical element may be a transparent element, whose thickness may be significantly larger than 30 μm. Further preferably, the prism may be a rotatable Dove prism. Advantageously, this provides an easy adjustment of alignment between the two GRIN elements and/or between either GRIN element and the corresponding optical fiber. Further, a rotatable Dove prism enables to rotationally align the off-axis cores of at least one of the two associated optical fibers. The additional optical element, such as a glass plate, may form the sterile barrier by itself, wherein neither GRIN element is sterile.

In another advantageous embodiment, a connector sleeve is provided for connecting an optical element of the optical arrangement with the fiber carrying unit. In this way, a secure mechanical connection between the optical element and the fiber carrying unit is formed, so that misalignment between the two associated optical fibers and/or between the optical arrangement and at least one of the two optical fibers is advantageously reduced. Preferably, the connector sleeve is a ceramic split mating sleeve.

In another advantageous embodiment, the gradient constants of two gradient index elements differ by less than a predefined value. In this way, the optical magnification factor of the two GRIN elements combined can be close to unity, which is advantageous for achieving low insertion loss. The predefined value may be between 0 and 10 percent, preferably between 0 and 5 percent, further preferably between 0 and 1 percent.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

In minimally invasive medical interventions, interventional devices such as needles, guide wires, sheaths and catheters are inserted in a patient in order to find and measure the relevant anatomy of the patient on one hand; and to treat or place a medical instrument such as a stent on the other hand. In such procedures, it is crucial that the part of the devices inserted into the patient either must be sterile during the entire procedure or should only be contaminated with fluids and/or tissues from the patient himself.

When the needle, guide wire or catheter is equipped with a sensor or activator, some connection must be made to transmit the information and/or power from the sensor to a controller or an interrogator and vice versa. The controller or interrogator is placed in the non-sterile zone away from the patient. Such a connection can be provided by an electrical wire or an optical fiber. Somewhere along the transmission line, the sterile zone meets the non-sterile zone. Therefore, proper management of sterility is required.

Optical shape sensing (OSS) uses back scattered infrared light along an optical fiber, in particular a multi-core optical fiber, to determine the strain along the length of the fiber. From the strain measurement in each of the cores of the multi-core optical fiber, the corresponding shape of that fiber can be reconstructed. When the optical fiber is incorporated into a flexible medical device such as guide wires or catheters this technology can provide the shape of the device within the patient's body.

The multi-core optical fiber used in OSS has a central core and multiple outer cores that spiral around the central core. This geometry poses additional challenges when the fiber has to be connected to another fiber which itself is connected to or inserted in an optical interrogator or a patch cord. Aside from centering both optical fibers to ensure a good coupling between the two central cores, proper rotational alignment must also be provided in order to connect the outer cores of the two optical fibers.

In order to provide an optical connection between the two optical fibers of the sterile side and the non-sterile side, respectively, and to enable a proper sterility barrier between the two fibers, one or more gradient index (GRIN) elements are used. GRIN elements or GRIN optical components have a gradual position-dependent variation in the refractive index which is advantageous for controlling the light propagation through the respective element.

GRIN optics may comprise a subset which consists of cylindrical components having a refractive index that changes only along the radial distance r. For instance, GRIN rod lenses have a radial refractive index profile that is essentially parabolic:

$$n(r) = n_0 \text{ sech } (gr) \approx n_0 \left(1 - \frac{g^2 r^2}{2}\right) \quad (1)$$

Here, g is the gradient constant, $n_0$ is the refractive index in the center of the lens, r is the radial position, and "sech" is the hyperbolic secant function. Light entering the GRIN rod lens is continuously refracted and the optical field inside such a GRIN rod lens is therefore periodically changing along the z-axis with a periodicity length of $z_{period}$:

$$z_{period} = \frac{2\pi}{g}. \quad (2)$$

A common way to describe the length of the GRIN rod lens is using the pitch P, which is the geometrical length L of the lens divided by the periodicity length $z_{period}$:

$$P = \frac{L}{z_{period}} = \frac{Lg}{2\pi}. \quad (3)$$

A GRIN rod lens which has a pitch of P=1, 2, 3, 4, . . . images its front plane onto its back plane and vice versa. GRIN rod lenses with a pitch of P=0.5, 1.5, 2.5, . . . also image the front plane onto the back plane, but the image is now inverted. Another typically used pitch value is P=1/4, 3/4, 5/4, . . . , wherein the GRIN rod lens ideally collimates the light from every point on its front plane.

Figure 1:
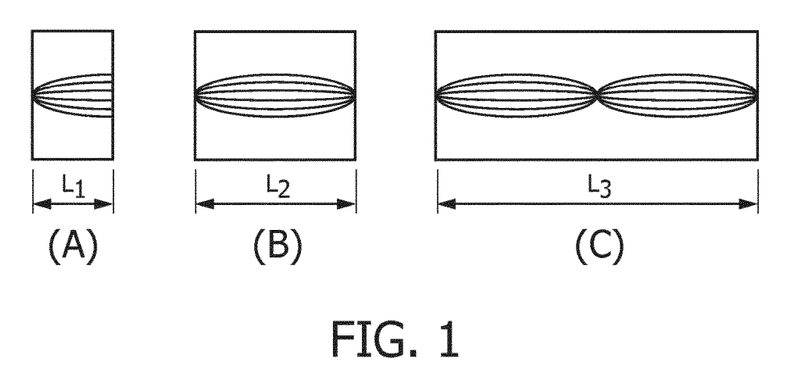
FIG. 1 shows an illustrative representation of three pitches each corresponding to a gradient index (GRIN) lens.

FIG. 1 shows three examples of GRIN rod lenses each having a different pitch value. In FIG. 1A, the length $L_1$ of the first GRIN rod lens is equal to a quarter of the periodicity length $z_{period}$ of the GRIN rod lens, resulting in a pitch value of P=0.25. In FIG. 1B, the length $L_2$ of the second GRIN rod lens is equal to a half of the periodicity length $z_{period}$, resulting in a pitch value of P=0.5. In FIG. 1C, the geometrical length $L_3$ of the third GRIN rod lens is equal to the periodicity length $z_{period}$, resulting in a pitch value of P=1.

The numerical aperture of a GRIN rod lens is defined by the refractive index at the center and the refractive index at the outer boundary of the rod lens:

$$NA = n_0 \sqrt{1 - \text{sech}^2\left(\frac{gd}{2}\right)}, \quad (4)$$

where NA is the numerical aperture of the GRIN rod lens and d is the diameter, preferably the outer diameter of the GRIN rod lens.

If the minimum required NA and the maximum diameter d are known, one is able to design a GRIN rod lens with a gradient constant g to fit different needs in the applications:

$$g = \frac{2}{d} \text{sech}^{-1}\left(\sqrt{1 - \left(\frac{NA}{n_0}\right)^2}\right). \quad (5)$$

When the required pitch P is further known, the geometrical length L, to which the GRIN rod lens is to be polished, can be determined to:

$$L = \frac{d\pi P}{\text{sech}^{-1}\left(\sqrt{1 - \left(\frac{NA}{n_0}\right)^2}\right)}. \quad (6)$$

Figure 2:
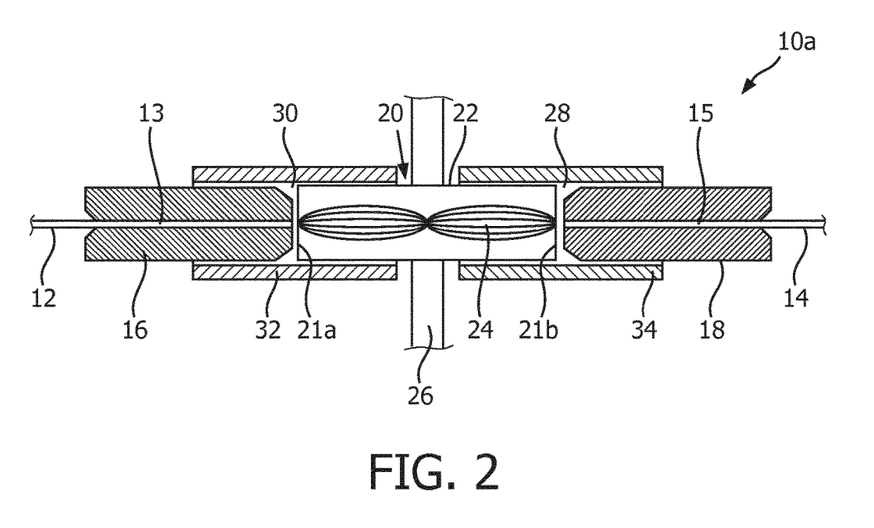
FIG. 2 shows a schematic diagram of a first embodiment of a medical optical connector.

FIG. 2 shows a medical optical connector 10a for reversibly connecting a first optical fiber 12 with a second optical fiber 14 for use in medical interventions. The medical optical connector 10a comprises a fiber carrying unit which consists of first ferrule 16 and a second ferrule 18. The first ferrule 16 is used for inserting an end portion 13 of the first optical fiber 12. The second ferrule 18 is used for inserting an end portion 15 of the second optical fiber 14.

The medical optical connector 10a comprises further an optical arrangement 20. The optical arrangement 20 consists of a gradient index (GRIN) lens 22. Preferably, the GRIN lens 22 has a pitch value of P=1 corresponding to the GRIN lens shown in FIG. 1C. The GRIN lens 22 is configured to interact with a light beam which comes from one of the first and second optical fibers 12, 14 and to conduct the light beam to the other one of the first and second optical fibers 12, 14, when the medical optical connector 10a is in a connected state, i.e. the two optical fibers 12, 14 are optically connected via the optical arrangement 20. The first and/or the second optical fibers 12, 14 may comprise multi-core optical fibers, wherein GRIN lens 22 is configured to optically couple the core(s) in the first optical fiber 12, 14 to the core(s) in the second optical fiber 14.

In minimally invasive medical interventions using optical shape sensing (OSS), one of the two optical fibers 12, 14 is connected to a controller, an interrogator and/or a patch cord placed in the non-sterile zone away from the patient, whilst the other one of the two optical fibers 12, 14 is incorporated into flexible medical devices such as guide wires, sheaths and/or catheters, which are then introduced into the body of the patient. For instance, the first optical fiber 12 is connected to the patch cord, controller or interrogator, thereby serving as an optical waveguide. The second optical fiber 14 may be incorporated into a flexible medical device such as a guide wire, a sheath or a catheter, thereby serving as an optical sensor.

Preferably, the first and the second optical fiber 12, 14 are each connected to the optical arrangement 20 by means of a connector sleeve 32, 34. The connector sleeves 32, 34 are provided with an inner space 30, 28 with an inner diameter so that both the outer part of the ferrules 16, 18 and the outer part of the optical arrangement 20, in particular the GRIN lens 22 are received by the inner space 30, 28. Preferably, the GRIN lens 22 is a GRIN rod lens. Further preferably, the GRIN rod lens 22 is mounted on a holder 26. Each optical fiber 12, 14 is encapsulated into the corresponding optic ferrule 16, 18. The outer diameter of the GRIN rod lens 22 is preferably matched to that of one or both ferrules 16, 18. The connector sleeves 32, 34 are preferably split mating sleeves. Advantageously, the connector sleeves 32, 34 improve the alignment between either optical fiber 12, 14 and the GRIN rod lens 22, thereby reducing the optical insertion loss of the optical connection.

Besides providing an optical connection between the two optical fibers 12, 14, the GRIN rod lens 22 also serves as the sterile barrier between the two optical fibers 12, 14. In this way, contaminations from the non-sterile side of the medical intervention, e.g. the optical waveguide, the patch cord, and the controller and/or the interrogator, can be prevented from entering the sterile side of the medical intervention, in particular the optical sensor, the flexible medical device such as the guide wire, the catheter or the sheath. Advantageously, the patient in treatment can be prevented from being contaminated from the environment. The holder 26 may serve as a part of the sterility barrier.

Preferably, the rotational alignment between the two optical fibers 12, 14 can be controlled using one or more keys on standard optical connectors and/or one or more key-slots in the mating sleeve. Further preferably, the GRIN lens is built with rotational symmetry with respect to the optical axis, so that it can be rotated in a random direction without influencing the imaging result.

The pitch P of the GRIN rod lens is preferably essentially equal to $$P = n/2, \quad (7)$$

where n is a positive integer, n=1, 2, . . . . In this way, the GRIN rod lens 22 acts as a relay lens that images its front surface 21a onto its back surface 21b and vice versa. The first ferrule 16, in which the end portion 13 of the first optical fiber 12 is inserted, may be arranged tightly towards the front surface 21a of the GRIN rod lens 22. Additionally or alternatively, the second ferrule 18, in which the end portion 15 of the second optical fiber 14 is inserted, may be arranged tightly towards the back surface 21b of the GRIN rod lens 22. In this way, the two optical fibers 12, 14 can be optically connected with each other. When the first and/or the second optical fibers 12, 14 are mechanically connected to the GRIN rod lens 22 sufficiently tightly so that there is essentially no free space between the optical fiber 12, 14 and the front and/or back surface 21a, 21b of the GRIN rod lens 22, the optical connection provided by the GRIN rod lens 22 is particularly stable and the physical connection makes that spurious reflections are dramatically reduced. Such a mechanically stable coupling is particularly advantageous in applications where the optical sensors have to be read out interferometrically, as is the case for OSS.

It is noted that the free space between either optical fiber 12, 14 and the front or back surface 21a, b of the GRIN rod lens 22 is sketched for better visibility and not representing actual distances between the components.

When n of Eq. (7) is an odd integer, the image plane of the GRIN rod lens 22 is inverted with respect to its object plane. The front/back surface corresponds to the object/image plane of the GRIN lens 22. In this case, the image plane can be brought to match the position and/or orientation of the first optical fiber 12 by simply rotating the second optical fiber 14 with respect to the first optical fiber 12 or vice versa. When n from Eq. (7) is an even integer, the two optical fibers 12, 14 may have the same orientation and do not need to be rotated relative to each other. A certain amount of minor rotation may still be needed in both cases (n being an odd or an even integer) in order to counteract any rotational misalignment between the two fibers.

In order to reduce the optical insertion loss of the medical optical connector 10a, it is crucial to achieve a proper alignment of the geometric center of either optical fiber 12, 14 and the optical axis of the GRIN rod lens 22. In order to do so, the connector sleeves 32, 34 are preferably ceramic split mating sleeves. Additionally or alternatively, the first and second ferrules 16, 18 are preferably standard ceramic fiber optic ferrules.

Further, the outer diameter of the GRIN rod lens 22 is configured to essentially match the outer diameter of the ceramic fiber optic ferrules 16, 18, so that the connector sleeves 32, 34, preferably the mating sleeves, are able to align the centers of the GRIN rod lens 22 and the fiber optic ferrules 16, 18.

If the pitch P of the GRIN rod lens 22 is chosen to be P=n/2 with n being an even positive integer (2, 4, 6, . . . ), the medical optical connector 10a is advantageously more tolerant against misalignment between the GRIN rod lens 22 and either fiber optic ferrules 16, 18. The reason is that the "object" provided by the first optical fiber 12 is imaged onto the "image" carried by the second optical fiber 14 by means of the GRIN rod lens 22 in a "4-f" configuration. The "4-f" configuration has a distance between the object plane and the image plane, wherein the distance is equal to four times of the focal length "f". If an object point is off-axis, the corresponding image point is also off-axis by the same amount as the object point and in the same direction with respect to the optical axis.

Besides the alignment between either fiber optic ferrule 16, 18 and the GRIN rod lens 22, it is also important to achieve a proper alignment between the two optical fibers 12, 14 themselves. This is of particular importance when optical fibers with off-axis cores are used, which is often the case in OSS. Preferably, standard solution of optical connectors comprising connector bodies such as SC or FC connectors may be applied. Similar to the way the ceramic split-sleeve is used in e.g. FC and SC connectors, we can use such sleeves in this connector 32, 34. Such connectors have usually a key that indicates the orientation of the optical fiber contained inside them. A mating sleeve with one or more key-slots on both sides may be used to fix the relative rotation between the two connector sleeves 32, 34. Preferably, the mating sleeve is modified to provide an extra space that is taken up by the GRIN rod lens 22. Further preferably, when the pitch of the GRIN rod lens 22 is P=n/2 with n=1, 3, 5 . . . , the key-slots on both sides of the mating sleeve should be reversed with respect to each other. The image carried by the cores from one of the two optical fibers is projected up-side-down in the other optical fiber on the other side of the GRIN lenses. Hence, the other optical fiber needs to be rotated with respect to the first optical fiber.

Preferably, the maximum optical insertion loss is in the order of 1 dB. For this purpose, the GRIN rod lens 22 is preferably configured with an outer diameter that varies by less than one micron from its target outer diameter, which is equal to the outer diameter of the ferrule and typically close to 2.5 mm. The outer diameter may depend on the numerical aperture (NA) of the optical fiber, wherein a lower NA indicates larger focus depth and a higher NA indicates shorter focus depth and tighter tolerances. This is the case for an odd or an even positive integer. Further, the GRIN rod lens 22 is preferably configured with a length which varies by typically less than 30 micron from its target length. In addition, the two ferrules 16, 18 are configured so that the lateral misalignment between the two fibers 12, 14 is less than one micron.

In FIG. 2, the optical arrangement 20 consists of a single GRIN rod lens 22. Alternatively, multiple GRIN rod lenses may be applied, wherein the total pitch, i.e. the sum of the individual pitch values of each of the individual GRIN rod lenses, is preferably sufficiently close to n/2, n being a positive integer, n=1, 2, 3, . . . . Further, the first and/or the second optical fiber 12, 14 may be a multi-core shape sensing optical fiber comprising a central core surrounded by a plurality of outer cores spiraling the central core along the elongation of the fiber. It is understood that the first optical fiber 12 may be used for the sterile side while the second optical fiber 14 for the non-sterile side or vice versa.

Figure 3:
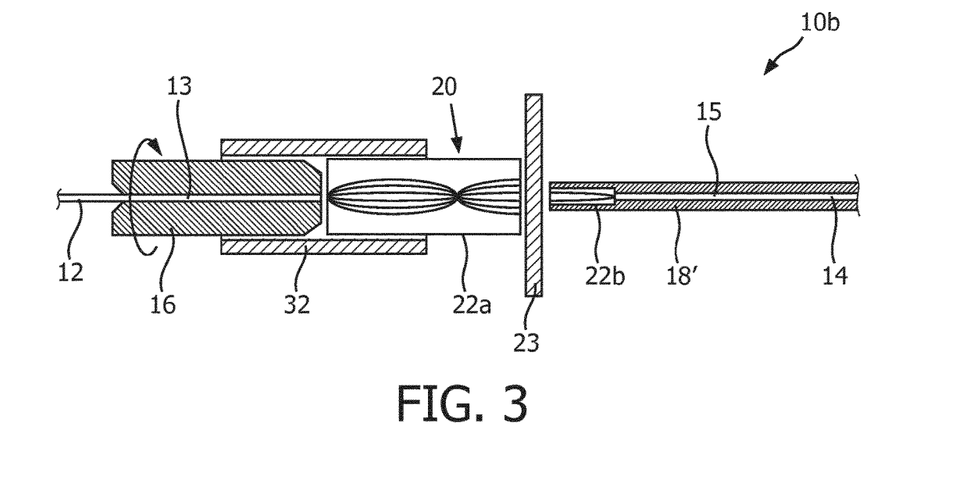
FIG. 3 shows a schematic diagram of a second embodiment of a medical optical connector.

FIG. 3 shows a medical optical connector 10*b* according to a second embodiment. The medical optical connector 10*b* is used for reversibly connecting two associated optical fibers 12, 14 for medical interventions, similar to the medical optical connector 10*a* shown in FIG. 2. The medical optical connector 10*b* comprises a first ferrule 16, in which an end portion 13 of the first optical fiber 12 is inserted or encapsulated. The optical arrangement 20 is also provided for interacting with a light beam from one of the optical fibers 12, 14 and conducting the light beam to the other one of the optical fibers 12, 14 in a connected state of the medical optical connector 10*b*.

In difference to the embodiment shown in FIG. 2, the optical arrangement 20 in FIG. 3 does not consist of a single GRIN rod lens, but a first GRIN rod lens 22*a* and a second GRIN rod lens 22*b* arranged along the optical axis of the first GRIN rod lens 22*a*. The first GRIN rod lens 22*a* is essentially the same as the GRIN rod lens 22 shown in FIG. 2, except for its pitch value. A ceramic split mating sleeve 32 is preferably provided to align the first ferrule 16 containing the end portion 13 of the first optical fiber 12 on one hand and the first GRIN rod lens 22*a* on the other hand, so that the center of the end portion 13 of the first optical fiber 12 is aligned to the optical axis of the first GRIN rod lens 22*a*.

The second GRIN rod lens 22*b* is integrated in a guide wire 18', in which an end portion 15 of the second optical fiber 14, preferably the entire second optical fiber 14, is inserted or encapsulated. The second GRIN rod lens 22*b* is connected to the end portion 15 of the second optical fiber 14. It is understood that the flexible medical device 18' may be a guide wire, a sheath and/or a catheter. Further, the flexible medical device 18' may be formed as part of the fiber carrying unit together with the first ferrule 16. Alternatively, the flexible medical device 18' may be a separate device from the medical optical connector 10*b*.

The pitch of the first and the second GRIN rod lens 22*a*, 22*b* is preferably essentially equal to $$P_i = (m_i/2 - 1/4), \tag{8}$$

where $m_i$ is a positive integer with $m_i=1, 2, \ldots$, and the index i denotes the first GRIN rod lens 22*a* (i=1) and the second GRIN rod lens 22*b* (i=2). Preferably, the values $m_i$ can be different for the first and second GRIN rod lenses 22*a*, 22*b*. As shown in FIG. 3, the value of $m_1$ for the first GRIN rod lens 22*a* is preferably 2, resulting in a pitch value of $P_1=3/4$. The value of $m_2$ for the second GRIN rod lens 22*b* is preferably 1, resulting in a pitch value of $P_2=1/4$.

Besides the pitch values, the two GRIN rod lenses 22*a*, 22*b* could also differ in their outer diameters. The outer diameter of the first GRIN rod lens 22*a* is preferably matched to that of the first ferrule 16, whilst the outer diameter of the second GRIN rod lens 22*b* is reduced to fit inside the flexible medical device 18', in particular a guide wire. Advantageously, this increases the back-loadability of the medical optical connector 10*b* since at least one side of the connector 10*b* has an outer diameter that is equal to or smaller than the outer diameter of the medical device 18'. Further advantageously, proper alignment between two optical fibers 12, 14 is simultaneously provided. In general, the outer diameter of the first GRIN rod lens 22*a* can be as large as needed in the medical application. Preferably, the larger outer diameter is at least twice, more preferably at least three times of the smaller outer diameter of the two GRIN lenses 22*a*, 22*b*.

The first GRIN rod lens 22*a* is preferably configured to receive and then collimate the light beam coming out from the first optical fiber 12. Subsequently, the second GRIN rod lens 22*b* preferably focuses the collimated light beam towards the second optical fiber 14. The first and/or the second optical fiber 12, 14 may be a multi-core optical fiber comprising a central core and a plurality of outer cores. In this case, the collimated light beam is preferably focused by the second GRIN rod lens 22*b* towards the plurality of outer cores and/or the central core of the second optical fiber 14 being a multi-core optical fiber.

Preferably, the first GRIN rod lens 22*a* is sterile so that it is able to serve as a sterile barrier. The two GRIN rod lenses 22*a*, 22*b* may be connected so that the distal end of the first GRIN rod lens 22*a* directly contacts the proximal end of the second GRIN rod lens 22*b*. Additionally or alternatively, a glass plate 23 or a thin transparent membrane may be arranged between the two GRIN rod lenses 22*a*, 22*b*, wherein the glass plate 23 or the membrane may act as the entire sterility barrier or part of it. The glass plate 23 is shown in FIG. 3, wherein the first GRIN rod lens 22*a* and/or the glass plate 23 form the sterility barrier of the medical optical connector 10*b*.

Since the light beam coming from either optical fiber 12, 14 can be collimated by the first GRIN rod lens 22*a* or the second GRIN rod lens 22*b*, respectively, the additional length of the optical path through the glass plate 23 or the membrane has advantageously no significant impact on the imaging performance thereby causing no additional insertion loss. For this reason, the glass plate 23 and/or the membrane may be significantly thicker than 30 microns in contrast to solution where no GRIN lenses are used.

Advantageously, an increased misalignment may be allowed between the first and the second optical fibers 12, 14 while maintaining the low optical insertion loss of the optical connection. In particular, the light beams are collimated at the interface between the two GRIN rod lenses 22*a*, 22*b*. Hence, a lateral shift between the two GRIN rod lenses 22*a*, 22*b* along the optical axis will therefore not cause a misalignment between the imaged light beams on the interface between the GRIN lens 22*b* and the fiber 15 and the core positions. In this way, the optical insertion loss is kept low. A boundary condition for a proper optical connection is that the fibers 12, 14 are well aligned with their respective GRIN lenses 22a, 22b. This alignment can for example already be done during assembly of GRIN lenses 22a, 22b with the fibers 12, 14 in a controlled environment.

Figure 4:
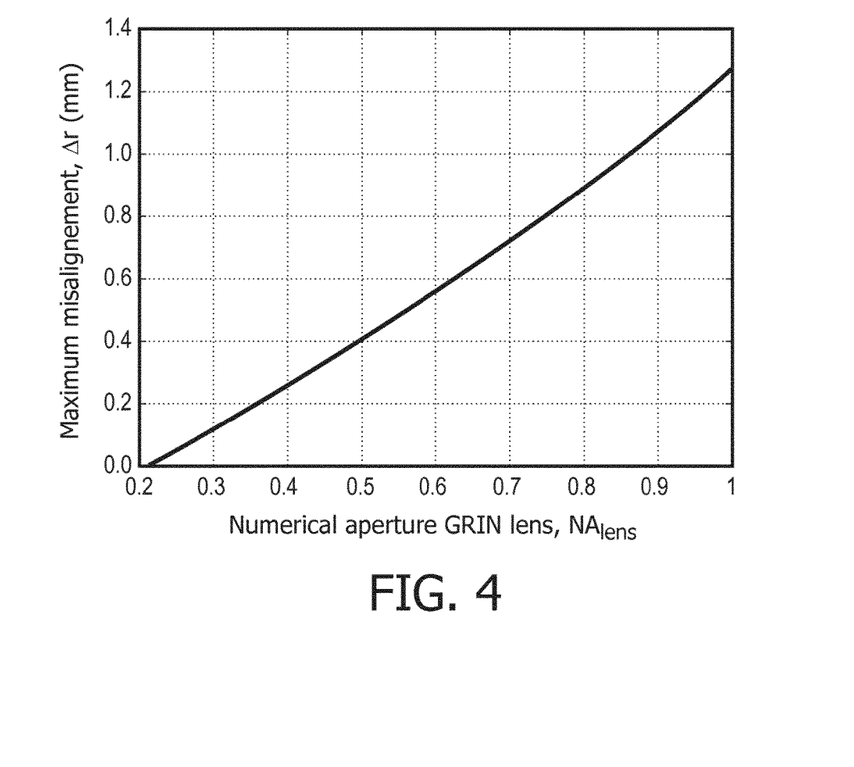
FIG. 4 shows a diagram, in which a maximum permissible misalignment is plotted against a numerical aperture of a GRIN lens of the medical optical connector shown in FIG. 3.

The amount of lateral misalignment Δr that can be tolerated between the two optical fibers 12, 14 without inflicting any significant insertion loss is equal to $$\Delta r = \frac{2}{g}\left(\text{sech}^{-1}\left[\sqrt{1-\left(\frac{NA_{lens}}{n_0}\right)^2}\right] - \text{sech}^{-1}\left[\sqrt{1-\left(\frac{NA_{fiber}}{n_0}\right)^2}\right]\right) \quad (9)$$

where $NA_{lens}$ is the numerical aperture of the second GRIN rod lens 22b that is integrated into the medical device 18', $NA_{fiber}$ is the numerical aperture of the optical fibers 12, 14, and g is the gradient constant of the lenses. At increased misalignment, light coming from the first optical fiber 14 may be directed so that it does not arrive at the second GRIN rod lens 22b, resulting in an insertion loss. The maximum value of allowed misalignment for a typical optical fiber with a numerical aperture of 0.21 and a GRIN rod lens with a gradient constant of g=0.95 mm$^{-1}$ is shown in FIG. 4 as a function of the numerical aperture of the second GRIN rod lens 22b.

Preferably, the maximum misalignment that is allowable between the two GRIN rod lenses 22a, 22b is a function of the numerical aperture of the GRIN rod lens with the smallest dimension, in particular outer diameter and/or length, i.e. the second GRIN rod lens 22b for the medical optical connector 10b. Additionally or alternatively, the maximum misalignment is a function of the numerical aperture of the GRIN rod lens that is integrated into the medical device 18'. Advantageously, the first and the second GRIN rod lens 22a, 22b may be configured to allow a large maximum misalignment between the two lenses 22a, 22b. At the same time, it is important to provide a proper alignment of the GRIN rod lenses 22a, 22b with respect to the optical fibers 12, 14. Preferably, the connector sleeve 32 may be a conventional mating sleeve, so that conventional alignment methods commonly used in optical connector assemblies can be applied to align the ferrules 16 and the first GRIN rod lens 22a on the non-sterile side of the optical connection, preferably on the patch cord side. Such a connector sleeve can usually be provided with any inner diameter so that it is able to receive the ferrule 16 and the first GRIN rod lens 22a.

On the sterile side, where the optical fiber 14 is integrated into the flexible medical device 18', in particular a guide wire, the second GRIN rod lens 22b needs to have an outer diameter that is limited by the lateral size of the medical device 18'. Preferably, the second GRIN rod lens 22b is directly spliced onto a proximal end of the second optical fiber 14 using commercially available splicing equipment. The proximal end refers to the end or end portion of an object, such as an optical fiber, elongated between the non-sterile side and the sterile side, wherein the proximal end faces or is part of the non-sterile side. Preferably, the whole medical device 18', for instance being a guide wire, including the second GRIN rod lens 22b is sterile. The distal end of an object elongated between a non-sterile side and a sterile side, such as an optical fiber, is the end that faces the sterile side. Additionally or alternatively, a GRIN multimode fiber can be used which has a sufficiently large core diameter such as 400 or 500 micron and is spliced directly to the proximal end of the second optical fiber 14. Advantageously, the misalignment between the second optical fiber 14 and the second GRIN rod lens 22b can be reduced to the order of 1 micron, for instance by using commercially available splicing machines or techniques.

While integrating the GRIN rod lens or GRIN multimode fiber directly into a guide wire, the outer diameter of the GRIN rod lens or the GRIN multimode fiber needs to be sufficiently small, in particular smaller than the GRIN rod lens that is used on the non-sterile side of the optical connection. At the same time, in order to keep the magnification of the two GRIN rod lenses combined close to unity, it is advantageous that the two GRIN rod lenses 22a, 22b have a sufficiently similar gradient constant g. In particular, the gradient constants g of the two GRIN rod lenses 22a, 22b differ by less than a predefined value, preferably less than 3%, more preferably less than 1%. For instance, the gradient constant of the two GRIN rod lenses 22a, 22b may be matched to that of the GRIN rod lens having a smaller thickness and/or the GRIN rod lens arranged on the sterile side/side of the interventional device. The optical magnification of the two GRIN rod lenses 22a, 22b combined differs from the value of 1 by preferably less than 3%, more preferably less than 1%.

In another advantageous embodiment, the length of the two GRIN rod lenses 22a, 22b combined and/or the gradient constant of the two GRIN rod lenses 22a, 22b depends more on the design parameters of the thinner GRIN rod lens from the two GRIN rod lenses 22a, 22b. In still a further embodiment where the optical arrangement 20 comprises three or more GRIN rod lenses, the total length and/or the total gradient constant of all gradient lenses combined preferably depends more on the design parameters of the thinnest GRIN rod lens compared to the other GRIN rod lenses.

Preferably, a mechanism is provided for mechanically rotating the first ferrule 16 in order to align the first and the second optical fiber 12, 14 with respect to each other. This mechanism could be a servo motor that rotates the first ferrule 16. Further, optical measurement signals may be used as a feedback signal to check the alignment achieved by the mechanism. Advantageously, the orientation of the medical device 18' such as a guide wire and/or the second optical fiber 14 can be known even after the guide wire and/or the optical fiber is inserted into the medical optical connector 10b. In this way, no key or marker is needed on the guide wire.

In another advantageous embodiment, a transparent material, such as a transparent glue, may be provided to the proximal end of the sterile device, in particular the second GRIN rod lens 22b, without affecting the coupling of the GRIN rod lens to the second optical fiber 14, in particular to the plurality of cores of the second optical fiber 14 being a multi-core optical fiber. The application of such transparent material is particularly easy due to the arrangement of the second GRIN rod lens 22b being integrated into the medical device 18'.

Figure 5:
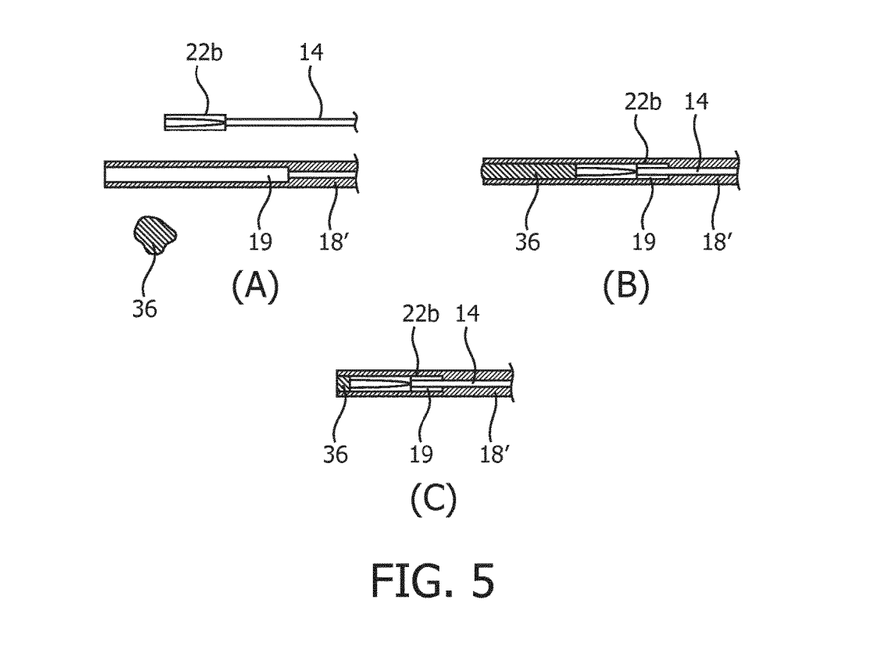
FIG. 5 shows a possible way of assembling the fiber and the GRIN lens into a medical device such as a guide wire, in particular a GRIN lens of the medical optical connector shown in FIG. 3, wherein a transparent glue is provided on one side of the GRIN lens.

FIG. 5A-C shows a possible method to mount the second optical fiber 14 together with the second GRIN rod lens 22b into a medical device 18', in particular a guide wire. In the proximal part of the guide wire 18', a cavity 19 is provided that is large enough to accommodate the GRIN rod lens 22b. The GRIN rod lens 22b may be spliced directly to the second optical fiber 14 to form an assembly which can then be inserted into the cavity 19 of the guide wire 18'. Preferably, the cavity 19 is large and/or long enough so that it is suitable for use with guide wires and optical fibers with different lengths.

In order to fill the remainder of the cavity 19 that is not occupied by the GRIN rod lens 22b or the optical fiber 14, a transparent glue may be provided in a small amount to that remainder of the cavity space. Preferably, the transparent material may be an optical-grade glue. Further preferably, the proximal end of the guide wire 18' may be polished after applying the transparent glue 36 in order to ensure high optical quality of the optical connection. These results in the assembly of the GRIN rod lens 22b and the optical fiber 14 inserted in the guide wire 18' shown in FIG. 5C. It is noted that as FIG. 5B, C shows, the cavity space 19 of the guide wire 18' is not fully filled by the assembly or the transparent glue 36. Alternatively, additional material, such as a transparent glue, may be applied to fully fill the cavity 19.

Figure 6:
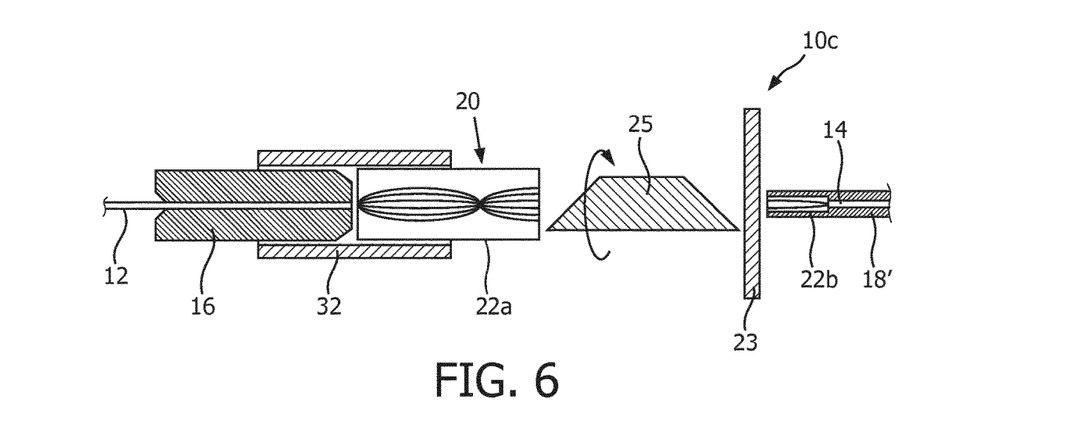
FIG. 6 shows a schematic diagram of a third embodiment of a medical optical connector.

FIG. 6 shows still a further embodiment of a medical optical connector 10c, which contains essentially the same components as the embodiment shown in FIG. 3, except that the optical arrangement 20 shown in FIG. 6 comprises an additional prism 25. Preferably, the prism 25 is a rotatable Dove prism which is arranged between the first GRIN rod lens 22a and the glass plate 23. It is noted that instead of the glass plate 23, a thin transparent membrane may be used. In this way, the possibility of a rotational alignment between the two optical fibers 12, 14 is provided without the need of rotating one of the two optical fibers 12, 14 with respect to the other optical fiber.

The two optical fibers 12, 14 may be connected randomly, wherein one or more cores of either optical fiber 12, 14 are arranged off-axis so that there is no need of knowing their exact relative orientation. The center core of the first optical fiber 12 is preferably arranged in the center of the first ferrule 16, so that the center core coincides with the optical axis of the GRIN rod lens 22a. The Dove prism 25 can then be rotated to align the first optical fiber 12 to the second optical fiber 14. Further, one can use optical measurement signals as a feedback signal to check the alignment between the two optical fibers 12, 14. It is noted that a misalignment due to an off-axis arrangement of the optical fiber 12, 14 cannot be compensated by the Dove prism 25.

Figure 7:
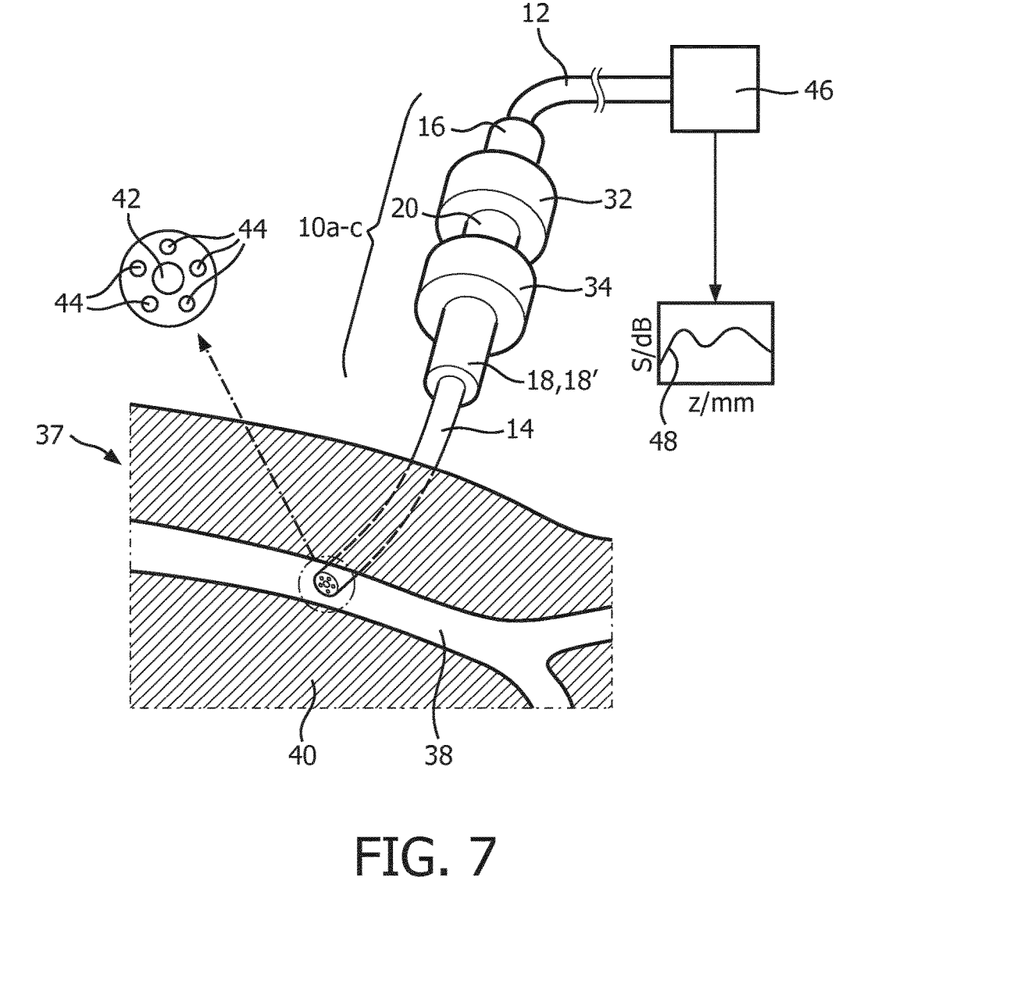
FIG. 7 shows a schematic diagram of a medical interventional device in use with a medical optical connector.

FIG. 7 shows a schematic diagram of the medical optical connector 10a-c in use with the first and the second optical fibers 12, 14. The medical optical connector 10a-c, the first and the second optical fibers 12, 14 form together an optical system, which is for optically coupling to an interventional medical device. The interventional medical device may be a catheter, a guide wire or a sheath. In FIG. 7, the interventional medical device is integrated with the second optical fiber 14. Alternatively, the interventional medical device may be a separate device optically connected to the second optical fiber 14.

The proximal end of the first optical fiber 12 is connected to an optical interrogator 46. The distal end of the second optical fiber 14 is inserted into a patient's body 37. The distal end of the first optical fiber 12 is inserted in the first ferrule 16, whilst the proximal end of the second optical fiber 14 is inserted in the second ferrule 18 or alternatively a guide wire 18'. In another advantageous embodiment, the entire second optical fiber 14 is inserted or encapsulated in a flexible medical device such as a guide wire, a sheath or a catheter, wherein the flexible medical device may be introduced into the body 37 of the patient.

The distal end of the second optical fiber 14 is arranged so that it is within a lumen 38 surrounded by tissues 40. As can be seen from the enlarged representation in FIG. 7, the second optical fiber 14 is a multi-core optical fiber comprising a central core 42 surrounded by a plurality of outer cores 44, preferably three outer cores 44. The second optical fiber 14 functions as an optical sensor which picks up optical signals, in particular reflectivity signals along the length of the fiber. These signals are then transmitted to the optical interrogator 46 via the optical arrangement 20 and the second optical fiber 12 serving as a waveguide. The optical interrogator 46 is configured to read out the optical signal, which is then transformed into position dependent signal represented by the curve 48 shown in the diagram of FIG. 7. Here, the position index is represented by z with the unit of mm, wherein the signal strength is represented by S with the unit of decibel.

The use of GRIN lenses may lead to additional reflections from the surfaces of the lenses. Such reflections may be minimized by matching the refractive index at the center of the GRIN lenses as well as possible to the refractive index of the optical fibers used in cooperation with the medical optical connector 10a-c. In particular, the refractive index at the center of the first and/or the second GRIN rod lenses 12, 14 differs from the refractive index of the first and/or the second optical fiber 12, 14 preferably by less than 1%. Further, the interfaces between at least one GRIN lenses on one hand and at least one optical fiber 12, 14 on the other hand may be polished so that the interface forms an angle with respect to the optical axis. In this way, the light reflected at the interface is not directed into the propagating mode of the optical fiber 12, 14. Preferably, the angle θ between the interface and the optical axis is in the range of $8° \leq \theta \leq 15°$. Additionally or alternatively, one or more anti-reflection coatings may be provided to the surface of at least one GRIN lens.

In an embodiment, the (average) refractive index of the lenses is chose to be sufficiently close to the refractive index of the fibers to reduce any reflections between their interfaces. In one example the GRIN lenses are made out doped quartz and used in combination of quartz fibers.

The reflected light intensity at a single interface between materials of refractive index $n_1=n$ and $n_2=n+\Delta n$, for $\Delta n$ small, is given by:

$$R = \left(\frac{n_2 - n_1}{n_2 + n_1}\right)^2 \approx \left(\frac{\Delta n}{2n}\right)^2$$

Typically one may want to reduce reflections to a level $R<10^{-6}$, hence with $n \approx 1.5$, then one finds that the index of fiber and lens materials should differ no more than $\Delta n < 3 \times 10^{-3}$.

Figure 8:
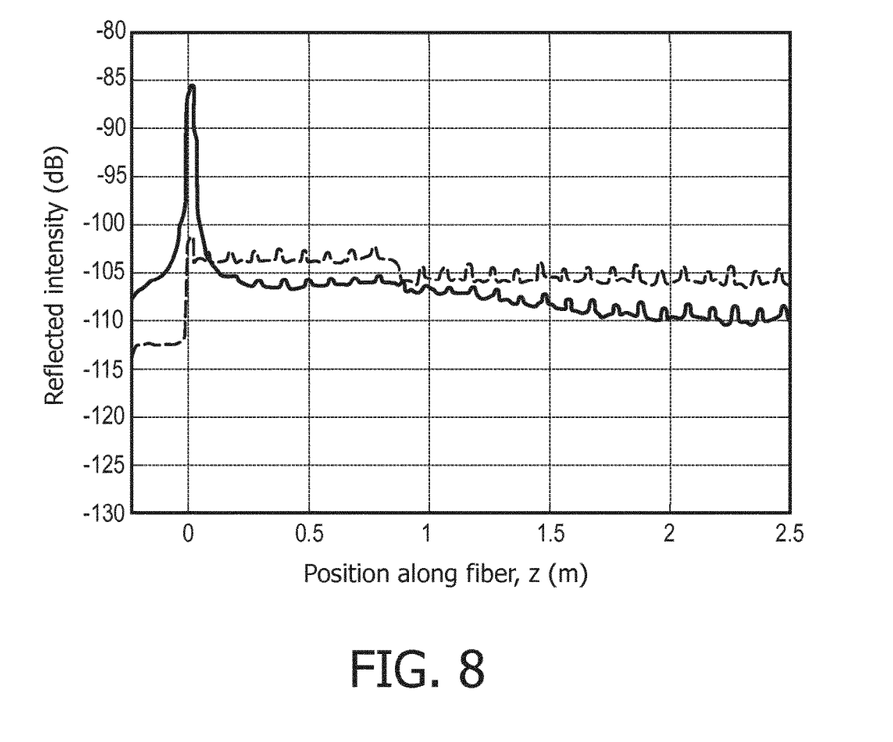
FIG. 8 shows a diagram with reflectivity measurement using the medical optical connector of FIG. 2 and using a conventional optical medical connector respectively.

FIG. 8 shows a diagram, in which the result of the reflectivity measurement is depicted as two curves. The solid curve has been obtained using the medical optical connector 10a shown in FIG. 2 comprising a GRIN lens; the dashed curve has been obtained using a conventional optical medical connector. The diagram shows the spatially resolved reflectivity signal in one of the off-center cores of the multi-core fiber.

An Optical Frequency Domain Reflectometer (OFDR) is used to optically interrogate a multi-core fiber that can be used for optical shape sensing, wherein the reflectometry and thus the optical interrogation is performed for the central core and each of the off-center cores separately. The result shown in FIG. 8 can be obtained using a system as shown in FIG. 7.

Both curves represent the reflectivity signal or reflected intensity with the unit of decibel as a function of the position index z along the off-center core of the multi-core optical fiber functioning as an optical fiber sensor with the unit of meter. The data shown in FIG. 8 have been smoothed over several centimeters for clarity.

The medical optical connector and hence the optical connection is located around z=0 where a multi-core patch cord is connected to a multi-core fiber sensor. There are multiple fiber Bragg gratings "written" along the length of the fiber sensor, wherein the reflection positions starting from z=0 in the positive direction are provided dominantly by these fiber Bragg gratings.

A combination of GRIN lenses is used such that the total pitch combined is P=1. In FIG. 8, it can be seen that the medical optical connector comprising the GRIN lenses gives a higher reflection peak at the position of the optical connection (z=0) compared to the conventional connector. This difference is mainly due to the mismatch in refractive index between the optical fiber and the GRIN lenses. Another effect of this mismatch is that there is an additional optical coupling loss in the case using GRIN lenses compared to the conventional connector. By better matching the refractive index of the GRIN lenses to the optical fiber, one can significantly improve the optical coupling and reduce the reflections. An improved matching in refractive index between the GRIN lenses and the optical fiber may for instance be achieved by using graded index fibers.

Figure 9:
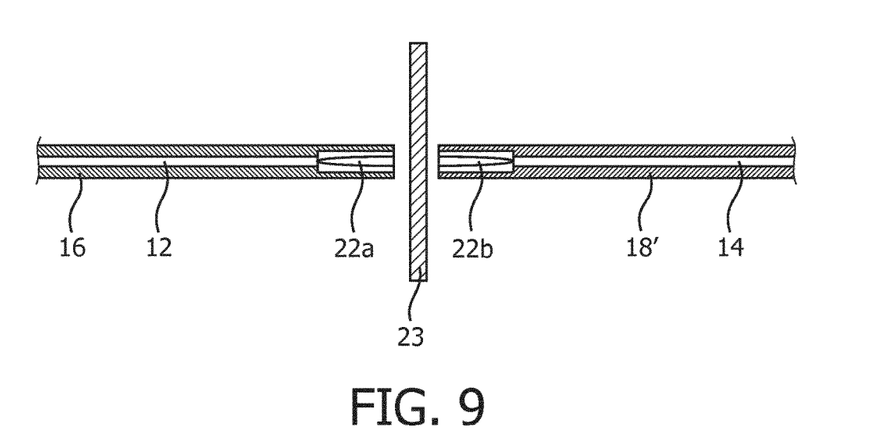
FIG. 9 shows a schematic diagram of a further embodiment of a medical optical connector.

FIG. 9 shows a further embodiment of a medical optical connector. Similar to the embodiment shown in FIG. 3 a medical device 18' is to be connected. As described in connection with FIG. 3, to minimize losses, the design of the smallest GRIN lens is leading in the determination of the lens length and the gradient constant. This constraint on the similarity of the gradient constant can be reduced by manufacturing a connection with two of the same GRIN lenses on both sides of the connector. So instead of having one GRIN lens larger than the other like in FIG. 3, in the embodiment of FIG. 9 both GRIN lenses 22a and 22b are of the same type with the same thickness and gradient constant. The length, which can be tuned with individual polishing of the lenses, can still be different.

As the diameter of the lenses on both sides of the connection is the same in this embodiment, they are now both constrained by the outer diameter of the medical device 18' in which GRIN lens 22b is integrated. This limited diameter means that it is hard to align the GRIN lens 22a to the fiber 12 with sufficient accuracy. However, this is solved in the same way as has been solved for the alignment between the GRIN lens 22b and the fiber 14 inside the medical device; namely by splicing them together in a controlled splicing machine. This splicing ensures a stable and precise alignment in both angle and position.

The additional optical element that provides for the sterile barrier, e.g. glass plate 23 or membrane layer of the embodiments shown in FIG. 3 and FIG. 9, fulfills a number of optical properties. First of all it is made of a material that is sufficiently transparent at its small thickness (typically less than a millimeter). This means that both scattering and absorption of the material is sufficiently low to limit insertion loss, and scattering alone is sufficiently low to limit crosstalk between the different cores of the multi-core optical fiber. Further, it has preferably a refractive index that is very close to that of the lenses, typically $\Delta n < 3 \times 10^{-3}$, similar to the difference in refractive index between fiber and lens, again to minimize reflection.

Then there are further advantageous properties of the additional optical element of the sterile barrier of combined optical and mechanical nature. A first such property is compressibility, which is very useful to compensate for small differences in polish angle and other surface irregularities of guide wire and ferrule (ferrule 16 in FIG. 9). Typical functional examples are given by polymer foils which deform under (soft) compression between guide wire and ferrule such that the sterile foil is in complete and perfect optical contact with both. A second property is to help prevent wear and scratching of the lens surfaces (of both guide wire and ferrule) during use, such as inserting of the guide wire and rotation of guide wire or ferrule to obtain optimum alignment of all cores of the multi-core fiber. Preferably any deformation of the sterile foil is of elastic and not of plastic nature, so that a sufficient number of reconnections can be made reliably during a medical procedure. From one procedure to the next, a new sterile foil must be inserted and any mechanical damage to the foil should be limited until replacement.

The medical optical connector 10a-c can be understood as "greater connector" which is used to bring together two optical connector ferrules. Such a "greater connector" includes extra functions in addition to an optical connection between the two optical fibers 12, 14, namely to support alignment, sterility, cleaning, loading of one or more components.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A medical optical connector for reversibly connecting two associated optical fibers for use in medical interventions, comprising:
   a fiber carrying unit configured to receive an end portion of at least one of the associated optical fibers, and
   an optical arrangement for interacting with a light beam from one of the associated optical fibers and conducting the light beam to the other one of the associated optical fibers in a connected state of the medical optical connector, the optical arrangement comprising two gradient index elements and an additional optical element arranged between the two gradient index elements and in direct contact with each of the two gradient index elements,
   wherein the additional optical element is replaceable,
   wherein the medical optical connector includes a sterility barrier between the associated optical fibers, and
   wherein the sterility barrier includes the additional optical element.

2. The medical optical connector of claim 1, wherein the sterility barrier further includes one of the gradient index elements.

3. The medical optical connector of claim 1, wherein a total pitch of the two gradient index elements is one.

4. The medical optical connector of claim 1, wherein the two gradient index elements have different pitches than each other.

5. The medical optical connector of claim 1, wherein at least one of the two gradient index elements comprises one of a gradient index lens and a gradient index fiber.

6. The medical optical connector of claim 1, wherein the two gradient index elements have different outer diameters.

7. The medical optical connector of claim 6, wherein a first one of the gradient index elements that has a smallest outer diameter is configured for integration in an interventional medical device, in which an end portion of a first one of the two associated optical fibers is insertable.

8. The medical optical connector of claim 7, wherein a second one of the gradient index elements that has a largest outer diameter is received by the fiber carrying unit, in which an end portion of a second one of the two associated optical fibers is insertable.

9. The medical optical connector of claim 6, wherein one of the two gradient index elements has an outer diameter equal to or smaller than an outer diameter of the interventional device.

10. The medical optical connector of claim 1, wherein the additional optical element comprises one of a glass plate, a membrane layer, and a prism.

11. The medical optical connector of claim 1, further comprising a connector sleeve for connecting an optical element of the optical arrangement with the fiber carrying unit.

12. An optical system for optically coupling to an interventional medical device, wherein the optical system comprises:
　　two optical fibers;
　　a medical optical connector for reversibly connecting the two optical fibers, wherein the medical optical connector includes:
　　　　a ferrule having disposed therein an end portion of a first one of the optical fibers,
　　　　a flexible device, comprising one of a guide wire, a sheath and a catheter, wherein the flexible device has disposed therein an end portion of a second one of the optical fibers, and
　　　　an optical arrangement for interacting with a light beam from one of the optical fibers and conducting the light beam to the other one of the associated optical fibers in a connected state of the medical optical connector, the optical arrangement comprising two gradient index elements and an additional optical element disposed between the two gradient index elements,
　　wherein a first one of the gradient index elements is disposed external to the ferrule and also external to the flexible device,
　　wherein a second one of the gradient index elements is disposed inside the flexible device,
　　wherein the additional optical element is disposed external to the ferrule and also external to the flexible device, and is replaceable,
　　wherein the medical optical connector includes a sterility barrier between the two optical fibers, and
　　wherein the sterility barrier includes the additional optical element.

13. The optical system of claim 12, wherein the additional optical element is in direct contact with each of the two gradient index elements.

14. The optical system of claim 12, wherein the sterility barrier further includes the first one of the gradient index elements.

15. The optical system of claim 12, further comprising a mating sleeve, wherein an end portion of the ferrule and an end portion of the first one of the gradient index elements are each disposed inside the mating sleeve adjacent to each other.

16. The optical system of claim 12, wherein a total pitch of the two gradient index elements is one.

17. The optical system of claim 12, wherein the flexible device comprises a catheter.

18. The optical system of claim 12, wherein the flexible device comprises a guide wire.

* * * * *